United States Patent
Baid

(10) Patent No.: US 8,235,945 B2
(45) Date of Patent: Aug. 7, 2012

(54) SAFETY DEVICE TO COVER THE NEEDLE TIP OF INTRAVENOUS CATHETER APPARATUS

(76) Inventor: Rishi Baid, New Delhi (IN)

(*) Notice: Subject to any disclaimer, the term of this patent is extended or adjusted under 35 U.S.C. 154(b) by 514 days.

(21) Appl. No.: 11/737,013

(22) Filed: Apr. 18, 2007

(65) Prior Publication Data

US 2008/0171986 A1 Jul. 17, 2008

Related U.S. Application Data

(60) Provisional application No. 60/804,214, filed on Jun. 8, 2006.

(51) Int. Cl.
*A61M 5/178* (2006.01)
*A61M 5/00* (2006.01)

(52) U.S. Cl. ............... 604/164.01; 604/110; 604/164.06

(58) Field of Classification Search .................. 604/110, 604/164.01, 164.08
See application file for complete search history.

(56) References Cited

U.S. PATENT DOCUMENTS

| | | | | |
|---|---|---|---|---|
| 5,051,109 A | * | 9/1991 | Simon | 604/263 |
| 5,328,482 A | * | 7/1994 | Sircom et al. | 604/164.08 |
| 5,447,501 A | * | 9/1995 | Karlsson et al. | 604/198 |
| 5,562,631 A | * | 10/1996 | Bogert | 604/192 |
| 6,224,569 B1 | * | 5/2001 | Brimhall | 604/164.08 |
| 6,443,927 B1 | * | 9/2002 | Cook | 604/110 |
| 6,749,588 B1 | * | 6/2004 | Howell et al. | 604/164.08 |
| 6,981,965 B2 | * | 1/2006 | Luther et al. | 604/110 |
| RE38,996 E | * | 2/2006 | Crawford et al. | 604/263 |
| 7,387,616 B2 | * | 6/2008 | Li | 604/198 |
| 7,458,954 B2 | * | 12/2008 | Ferguson et al. | 604/110 |
| 7,507,222 B2 | * | 3/2009 | Cindrich et al. | 604/198 |
| 2002/0107483 A1 | | 8/2002 | Cook | |
| 2004/0116855 A1 | * | 6/2004 | Popov et al. | 604/110 |
| 2004/0162526 A1 | * | 8/2004 | Vaillancourt et al. | 604/192 |
| 2005/0277879 A1 | * | 12/2005 | Daga | 604/110 |

FOREIGN PATENT DOCUMENTS

| | | |
|---|---|---|
| EP | 1 491 224 A1 | 12/2004 |
| WO | WO 01/23029 A | 4/2001 |
| WO | WO 01/93940 A | 12/2001 |

OTHER PUBLICATIONS

Baid, Rishi, International Search Report, PCT/US2007/009539 filed Apr. 18, 2007, 5 pages.

* cited by examiner

*Primary Examiner* — Nicholas Lucchesi
*Assistant Examiner* — Ian Holloway
(74) *Attorney, Agent, or Firm* — Kilpatrick Townsend & Stockton LLP

(57) ABSTRACT

A safety device for the needle of intravenous catheter apparatus comprising of a tip blocker which blocks the needle tip, a spring assembled in compressed state held by a disc inside the groove of the tip blocker which pushes the tip blocker downwards and a bush fitted in the needle passageway which does not allow the needle to come out of the safety device. The safety device is capable of locking inside it and covering the needle tip so that the needle of intravenous catheter apparatus can be disposed of safely.

5 Claims, 8 Drawing Sheets

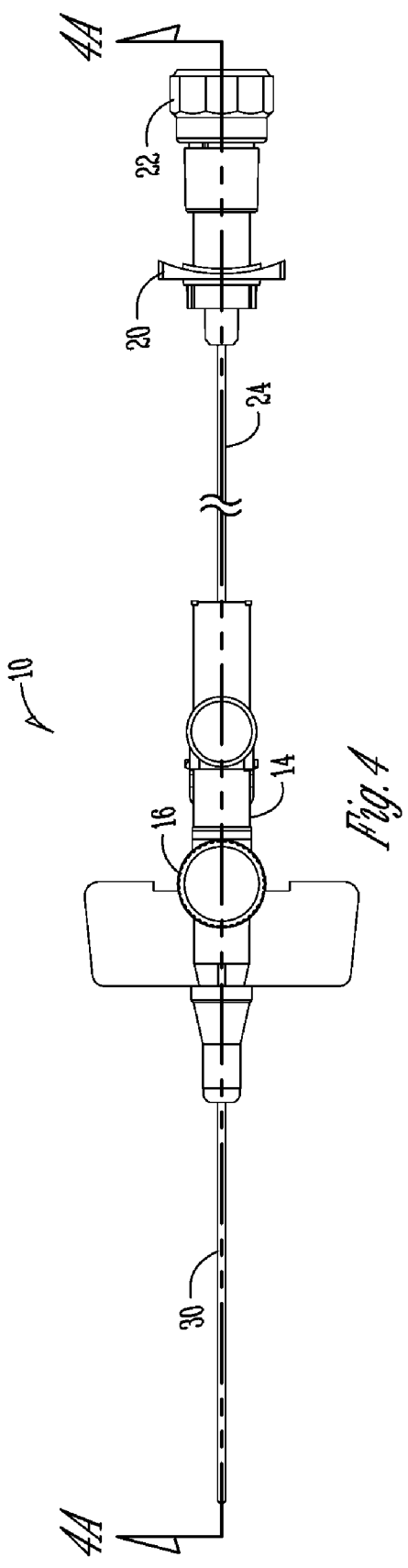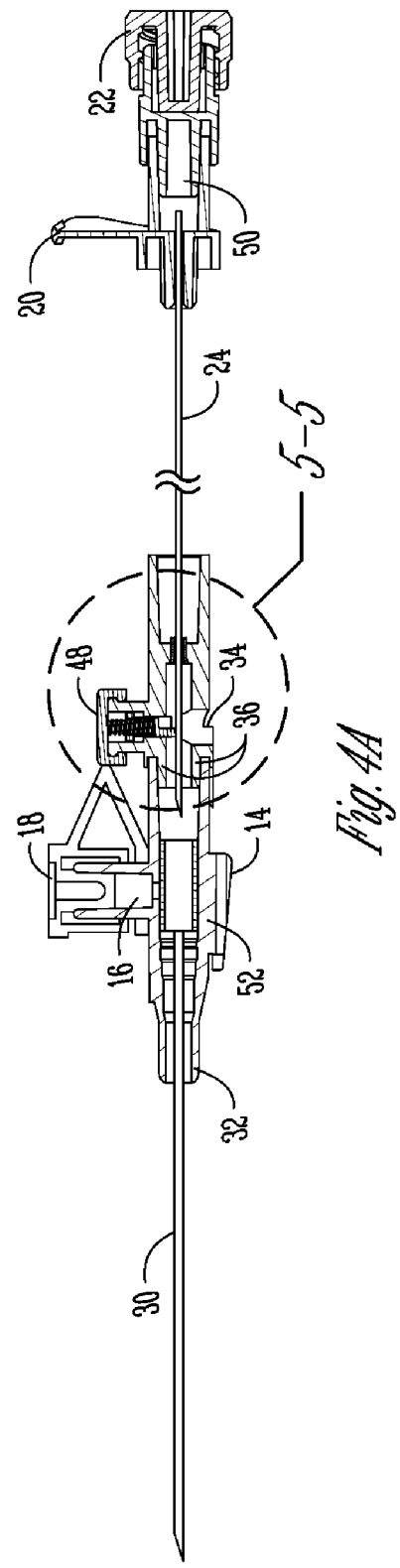
Fig. 4
Fig. 4A

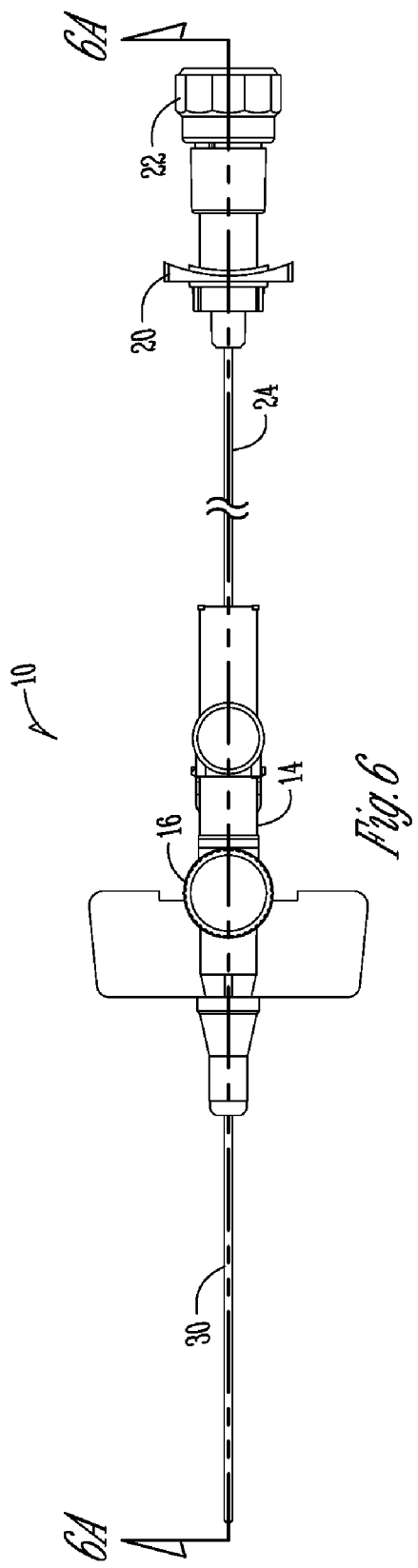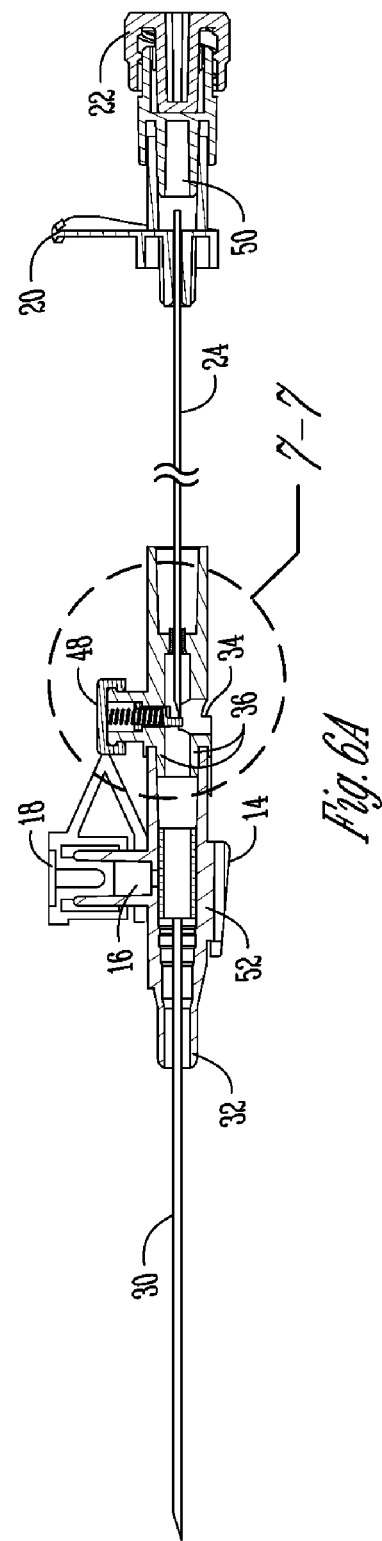

SAFETY DEVICE TO COVER THE NEEDLE TIP OF INTRAVENOUS CATHETER APPARATUS

CROSS-REFERENCE TO RELATED APPLICATIONS

This application claims priority under 35 U.S.C. §119 of a provisional application Ser. No. 60/804,214 filed Jun. 8, 2006, which application is hereby incorporated by reference in its entirety.

FIELD OF INVENTION

The present invention relates to a safety device for the needle of an intravenous catheter apparatus. More particularly this invention relates to a safety device fitted to an intravenous catheter apparatus which covers the needle tip after use, prior to the needle being disposed of, thereby preventing accidental pricking of the used needle of the intravenous catheter apparatus by medical professionals, people in charge of disposal of hospital waste and anybody who accidentally or intentionally handles or tries to dispose of the intravenous catheter apparatus.

BACKGROUND OF INVENTION

The intravenous catheter apparatus is used to inject medicines, glucose and other nourishment, in liquid form, into the blood stream of patients during their treatment. Such intravenous catheter apparatuses are known from the prior art and permit the inlet of different media flow during the treatment of the patient. After the needle along with a flexible catheter is inserted in the vein of the patient and blood flashes in the catheter, the needle is withdrawn from the vein. The flexible catheter portion continues to remain in the vein to inject medicines, glucose and other nourishment in liquid form into the blood stream. The needle is disposed of after withdrawal from the catheter and the vein. If the used needle is not covered with some protection, it can prick anyone who comes into contact with the needle, including medical professionals and people in charge of disposal of hospital waste. Accidental pricking by used needles is very dangerous and at times even fatal if the needle has come into contact with the blood of an ill patient. Accidental pricking may spread blood borne diseases like Hepatitis B, AIDS, etc. In view of the foregoing, a safety device is essential to completely cover the tip of the needle after use and while disposing it to thereby prevent contact with the needle.

The prior art acknowledges the need for a needle tip guard placed upon the needle after it's been withdrawn from the catheter. For example, U.S. Pat. No. 5,135,504 uses a needle safety device in which a "retaining ring" is fitted inside the intravenous catheter apparatus and the "needle guard" slides inside the retaining ring. This device has some of the following disadvantages: 1) the retaining ring remains inside the main body during use of the apparatus which hinders flow of solutions through it, 2) there is a likelihood that guard jaws which cover the needle tip may open so as to expose the needle tip, 3) there is chance that blood on or near the needle tip may surface out of the needle guard because the needle is still exposed from the sides and because the size of the needle guard is too small with respect to the portion of the needle needing to be covered.

In other prior art references such as U.S. Pat. No. 6,117,108, the safety device remains inside the main body of the catheter apparatus. However, because of the miniature size of the main body there remains a strong probability of blood coming out of the safety device and infecting the persons handling the used needle.

OBJECTS OF INVENTION

A primary object of this invention is to propose a safety device for the needle of an intravenous catheter apparatus that facilitates and ensures safe disposal of the needle of the intravenous catheter apparatus after the needle is withdrawn from the vein of a patient following cannulation.

Another object of this invention is to propose a safety device for the needle of an intravenous catheter apparatus in which the disadvantages of prior art are overcome.

Another object of this invention is to propose a safety device for the needle of an intravenous catheter apparatus, which securely locks the needle tip so that the needle may not be pushed or pulled out of the safety device.

A further object of this invention is to propose a safety device for the needle of an intravenous catheter apparatus, which is big enough to cover the needle tip from all sides thereby preventing infected blood from oozing out of the safety device.

Yet another object of this invention is to propose a safety device for the needle of an intravenous catheter apparatus which may be fitted between a wing body and needle hub in such a way that it does not create any impediment to the function and operation of the intravenous catheter apparatus.

Still another object of this invention is to propose a safety device for the needle of an intravenous catheter apparatus, which is externally attached to the body of the apparatus so that no part remains inside the apparatus to affect the flow of liquid through the apparatus.

A further object of this invention is to propose a safety device for the needle of an intravenous catheter apparatus, which requires only slight force to detach it from the wing body, without disturbing the position of the catheter.

Still another object of this invention is to propose a safety device for the needle of an intravenous catheter apparatus, which can be easily assembled and involves a simple structural configuration.

Another object of this invention is to propose a safety device for the needle of an intravenous catheter apparatus which is economical to produce.

SUMMARY OF THE INVENTION

The present invention consists of safety device for the needle of an intravenous catheter apparatus, which is provided between the wing housing and the needle hub of an intravenous catheter apparatus. After the needle along with the flexible catheter is inserted in vein of the patient and blood flashes in the catheter, the needle is withdrawn from the vessel holding the wing housing. The needle bug along with the needle moves out of the catheter and thereafter passes through the wing housing and reaches the safety device. As soon as the needle tip moves past the tip-blocker, the tip-blocker is forced downward, due to the pressure of the spring, in front of the needle tip. Thus, the tip blocker blocks and prevents the needle tip from moving forward in the direction of the catheter. When the needle is further withdrawn, the flaring near the tip of the needle prevents the needle from being pulled out of the safety device. In this position, the needle can neither move inward nor outward and is totally locked inside the safety device. If further force is applied in the outward direction to withdraw the needle, the safety device detaches itself from the wing housing and the needle hub assembly, such that the needle and safety device together separate from the wing assembly. The needle can now be safely disposed of as the needle tip is locked inside the safety device in such a way that it cannot be pushed or pulled out of the safety device.

BRIEF DESCRIPTION OF THE DRAWINGS

FIG. 4 is a top view of the intravenous catheter apparatus with the needle partially removed from the catheter and wing housing.

FIG. 4A is a cross sectional view of the apparatus of FIG. 4 taken along line 4A-4A.

FIG. 6 is a top view of the intravenous catheter apparatus with the needle pulled out of the wing housing and locked in the safety device.

FIG. 6A is a cross sectional view of the apparatus of FIG. 6 taken along line 6A-6A.

DETAILED DESCRIPTION OF THE PREFERRED EMBODIMENT

Figure 1:
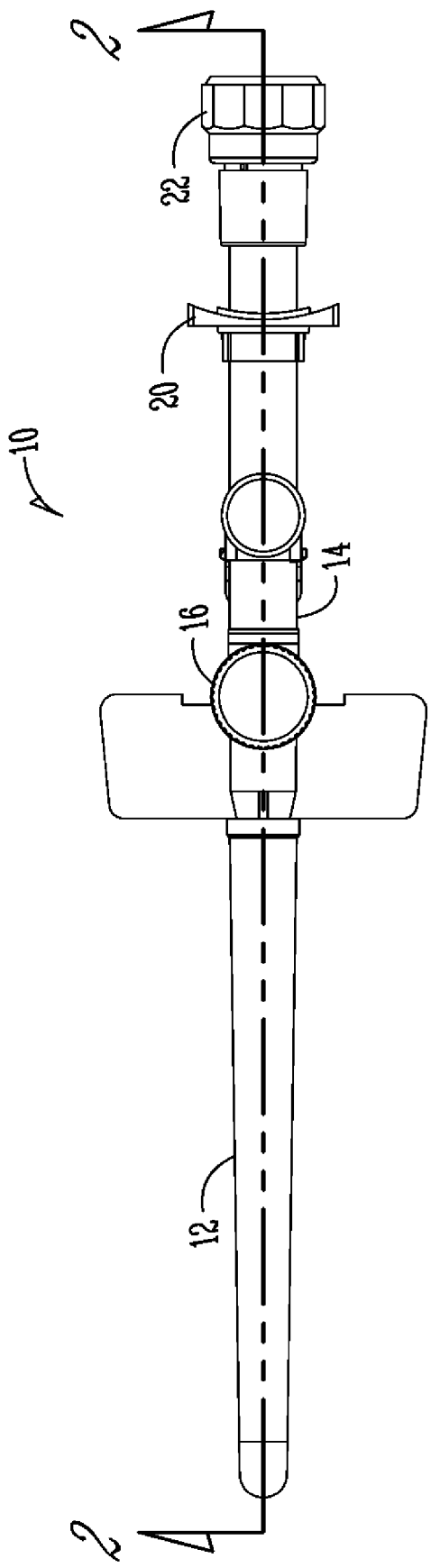
FIG. 1 is a top view of an intravenous catheter apparatus.

Referring to FIG. 1, an intravenous (IV) catheter apparatus 10 of the present invention is shown. It comprises of needle cover 12, wing housing 14, port 16 in unitary assembly with the wing housing 14 and needle hub 20. Luer lock 22 is removably attached to wing housing 14. The needle cover 12 covers the needle 24 (shown in FIG. 2). The needle hub 20 can be detached from the wing housing 14 such that the assembly of needle 24, needle hub 20 and luer lock 22 can be separated from the assembly of wing housing 14 and port 16, such as shown in FIG. 8A.

Figure 2:
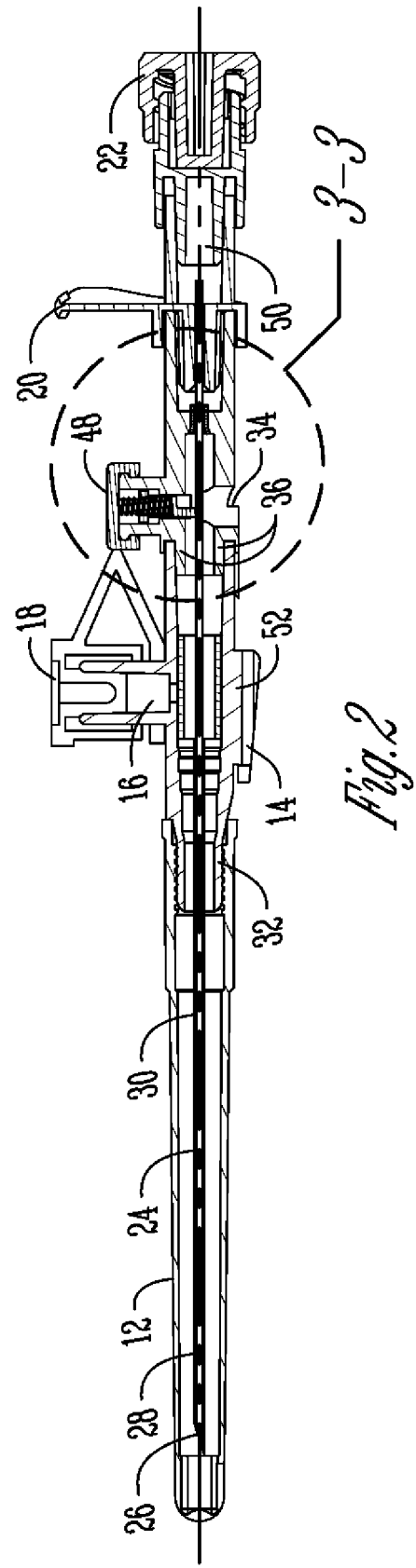
FIG. 2 is a cross sectional view of the apparatus of FIG. 1 taken along line 2-2.

FIG. 2 is a cross sectional view of the IV catheter apparatus 10 which depicts a needle 24 extending from needle hub 20 through the wing housing 14 and ending at the needle tip 26 under the needle cover 12.

The needle 24 is hollow and the needle tip 26 is cut diagonally. There is needle flaring 28 which increases the diameter of the needle 24 near the needle tip 26. Surrounding the needle 24 is a catheter 30 which is attached to the wing housing 14 at the catheter base 32. The catheter 30 is a flexible tube which is placed in the vein of a patient to provide fluids, nourishment and medicines. Wing housing 14 has a port 16 covered by port cap 18 through which fluid, nourishment or medicines are injected which travel through wing housing 14 and catheter 30 into the patient's vein. The safety device 34 is located between wing housing 14 and needle hub 20 and is aligned in the vertical plane along the plane of port cap 18 and needle hub 20. Two lugs 36 removably hold the safety device 34 to the wing housing 14.

Figure 3:
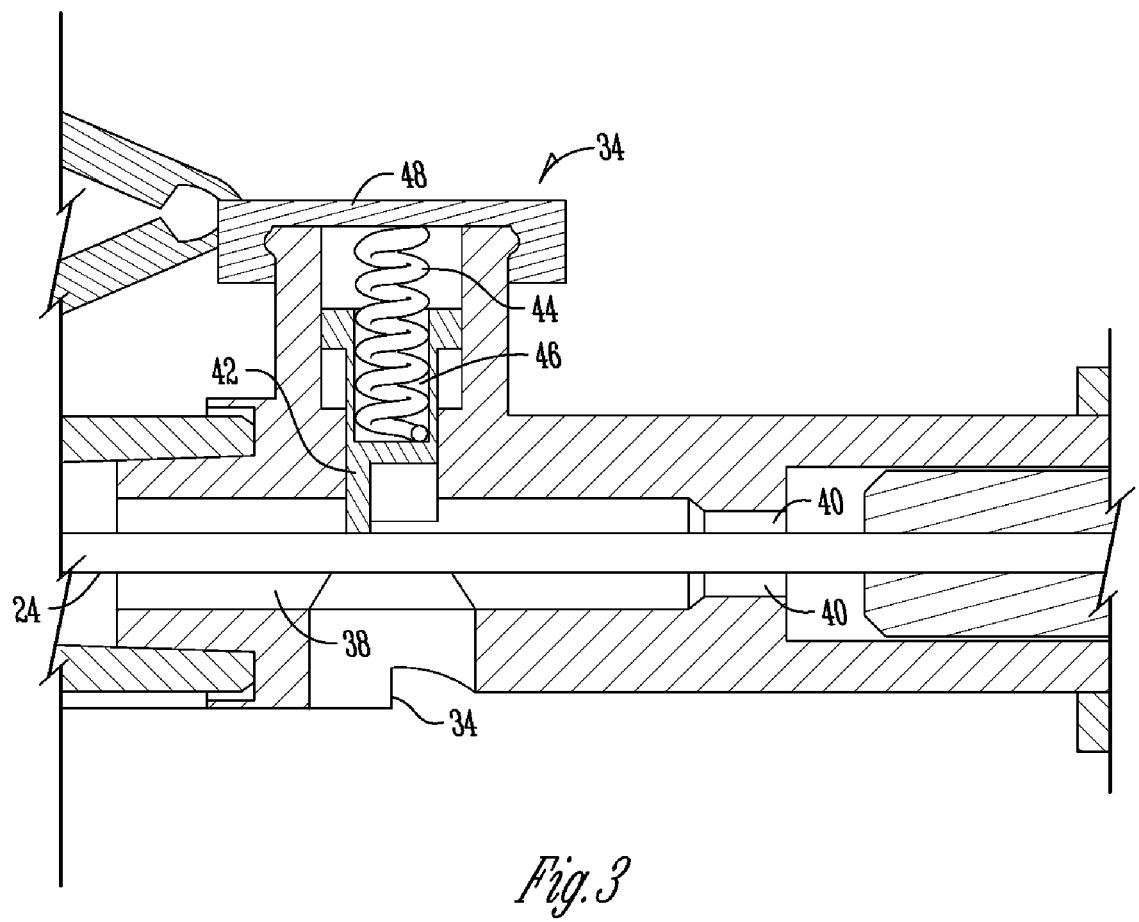
FIG. 3 is an enlarged view of section 3-3 of FIG. 2.

FIG. 3 is the enlarged cross sectional view of the safety device 34 of FIG. 2. The needle 24 passes through the needle passageway 38 and bush 40 inside the safety device 34. The safety device 34 has a tip blocker 42 which blocks the needle tip 26. A spring 44 is arranged in a compressed state inside the groove 46 of the tip blocker 42 and is held in such position by a disc 48.

To use the IV catheter apparatus 10 the needle cover is removed and the needle 24 along with catheter 30 is inserted into the patient's vein. Because the blood within the vein is under pressure, as soon as needle tip 26 punctures the skin and enters the vein, blood gushes up into the hollow needle 24 and through the wing housing 14 until it reaches the flash back chamber 50 shown in FIGS. 2, 4A, 6A and 8A. The needle 24 is then withdrawn out of the vein and the catheter 30 by pulling the needle hub 20 away from the wing housing 14. The needle 24 passes through catheter base 32 and silicon tube 52.

FIG. 4 shows the top view of the IV catheter apparatus 10 when the needle 24 is partially withdrawn form the wing housing 14. The cross section of FIG. 4A shows clearly that the needle 24 has moved past the catheter 30, the catheter base 32 and the silicon tube 52 such that the diagonal cut portion of needle tip 26 is being withdrawn toward the safety device 34.

Figure 5:
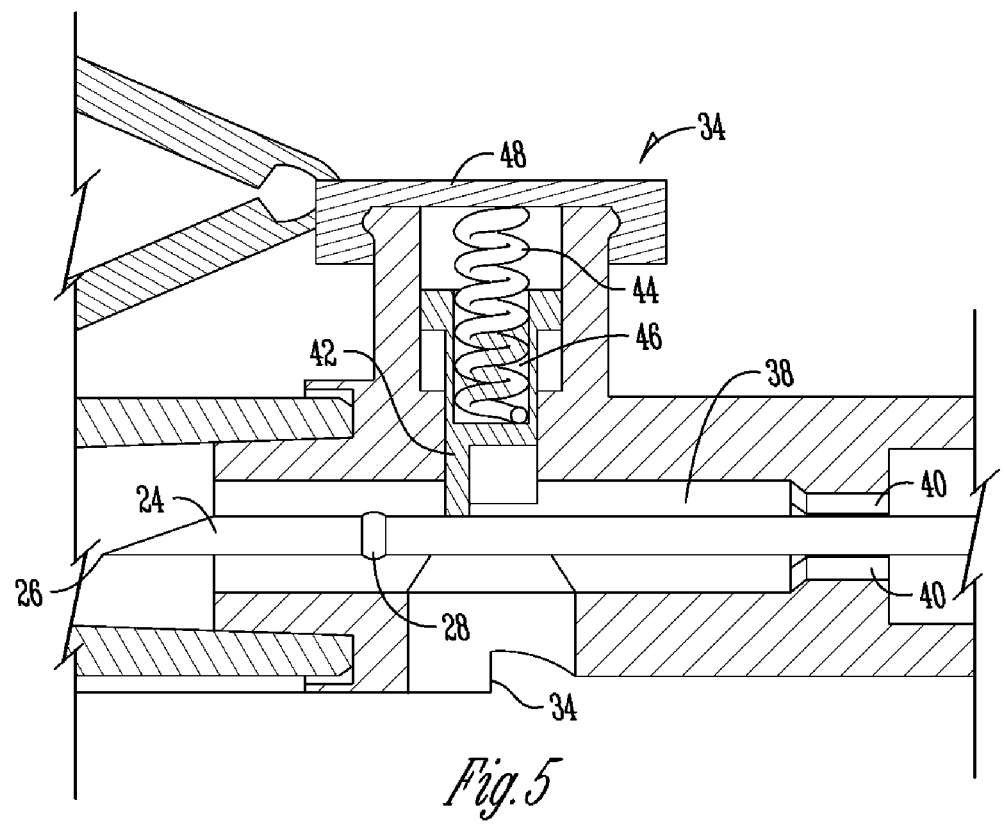
FIG. 5 is an enlarged view of section 5-5 of FIG. 4A.

FIG. 5 is the enlarged cross sectional view of the safety device 34 of FIG. 4. FIG. 5 depicts the needle 24 touching the tip blocker 42 and passing through the bush 40. Needle flaring 28 near the tip blocker 42 is also shown. The spring 44 is shown in the compressed position. In this position, the spring 44 exerts downward pressure on the tip blocker 42.

Figure 5A:
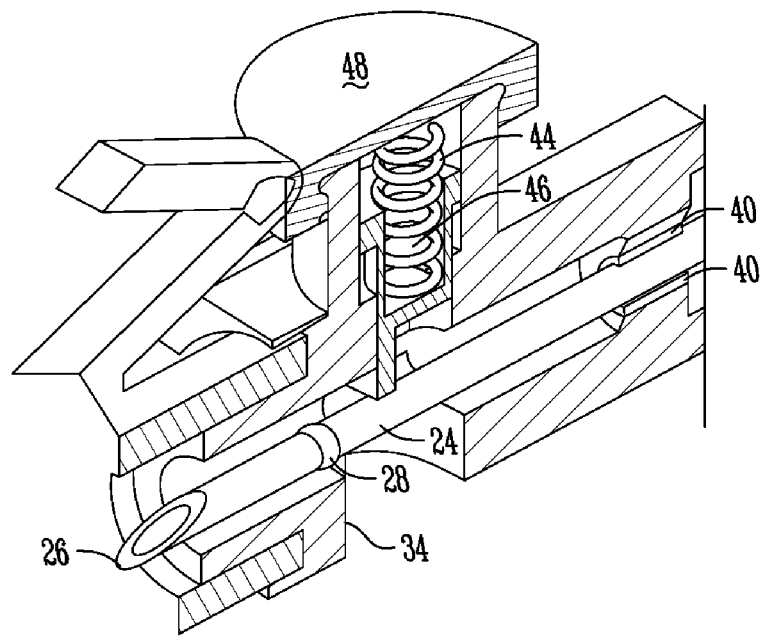
FIG. 5A is an isometric view of section 5-5 of FIG. 4A.

FIG. 5A provides an isometric view of FIG. 5 showing the parts of the wing housing 14, namely the needle tip 26, needle flaring 28, tip blocker 42 and bush 40.

FIG. 6A is a cross sectional view taken along line 5-5 of FIG. 6. FIG. 6A shows the needle tip 26 being blocked by the tip blocker 42 preventing any forward movement of the needle tip 26 within the safety device 34. By pulling the needle hub 20 the needle 24 and needle tip 26 moves past the tip blocker 42; the tip blocker 42 falls down under the pressure of compressed spring 44 and enters the needle passageway 38, which blocks the needle passageway 38.

Figure 7:
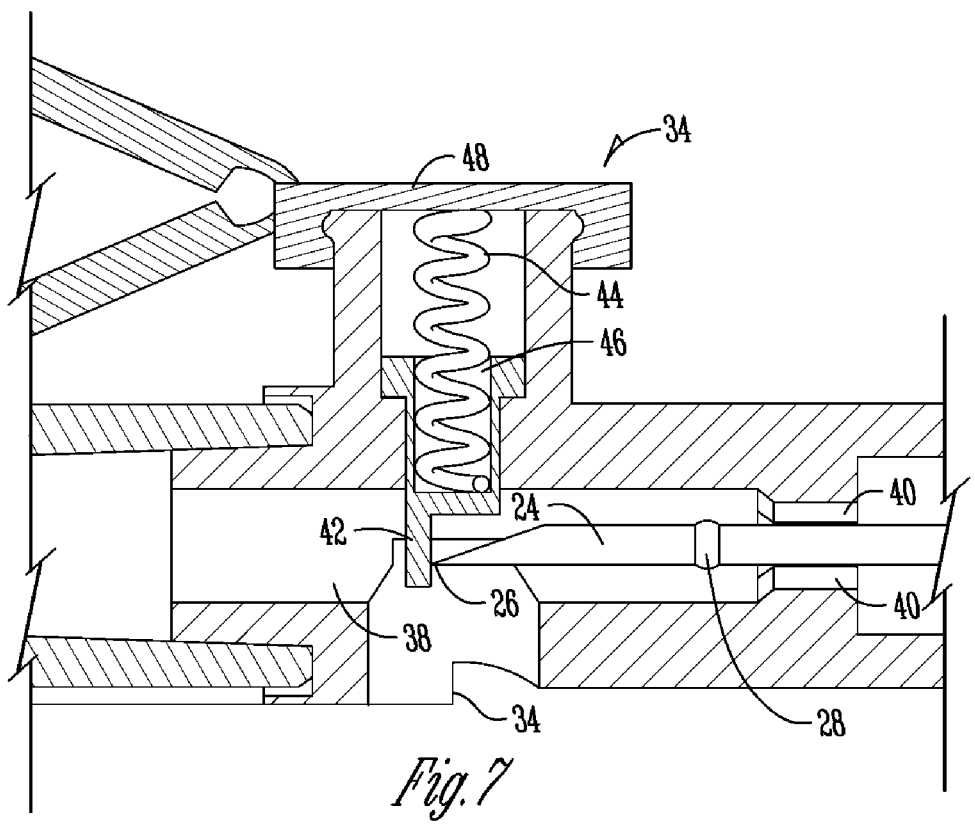
FIG. 7 is an enlarged view of section 7-7 of FIG. 6A.
Figure 7A:
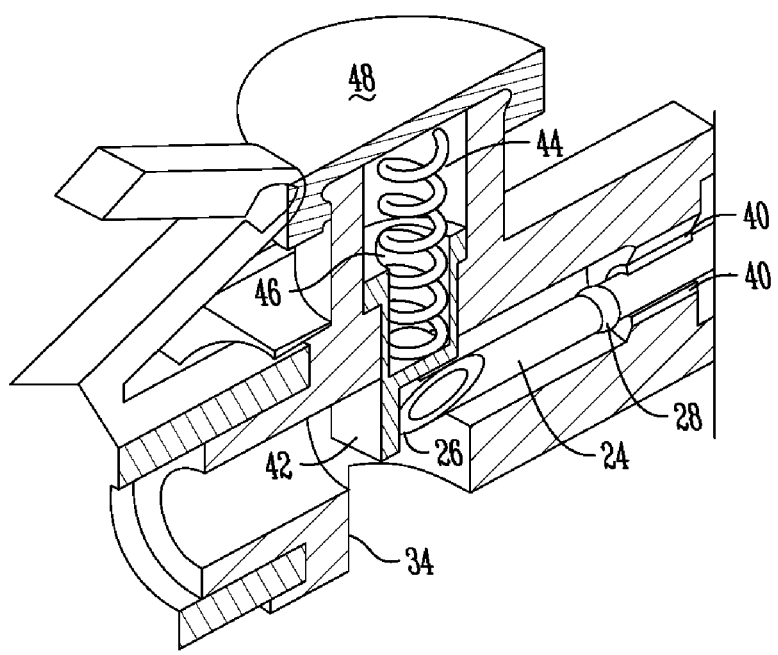
FIG. 7A is an isometric view of section 7-7 of FIG. 6A.

FIG. 7 is an enlarged cross sectional view taken along line 7-7 of FIG. 6A. FIG. 7 shows how the spring 44 has moved tip blocker 42 into the needle passageway 38 thereby blocking any forward movement of the needle tip 26. In this position, the needle tip 26 cannot move outside the wing housing 14. The location of needle flaring 28 and position of bush 40 is fixed in such a way that when the tip blocker 42 comes down, the needle flaring 28 is inside the safety device 34 in front of the bush 40. FIG. 7A shows an isometric view of the constituent parts of the safety device 34 namely, tip-blocker 42 blocking needle tip 26, flaring 28 and bush 40.

Figure 8:
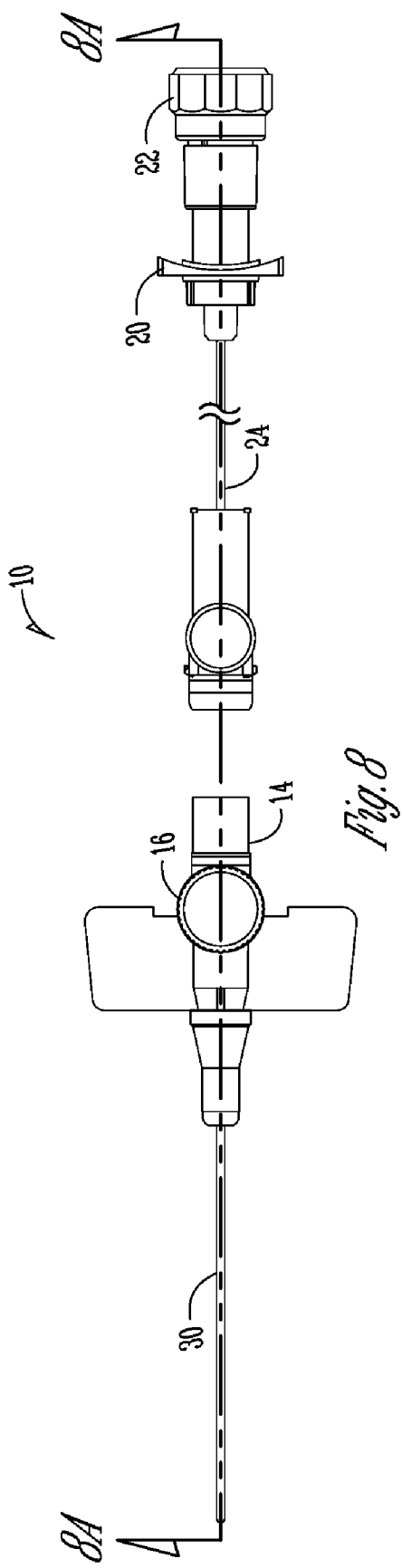
FIG. 8 is a top view of the intravenous catheter apparatus with needle along with safety device detached from the wing housing.
Figure 8A:
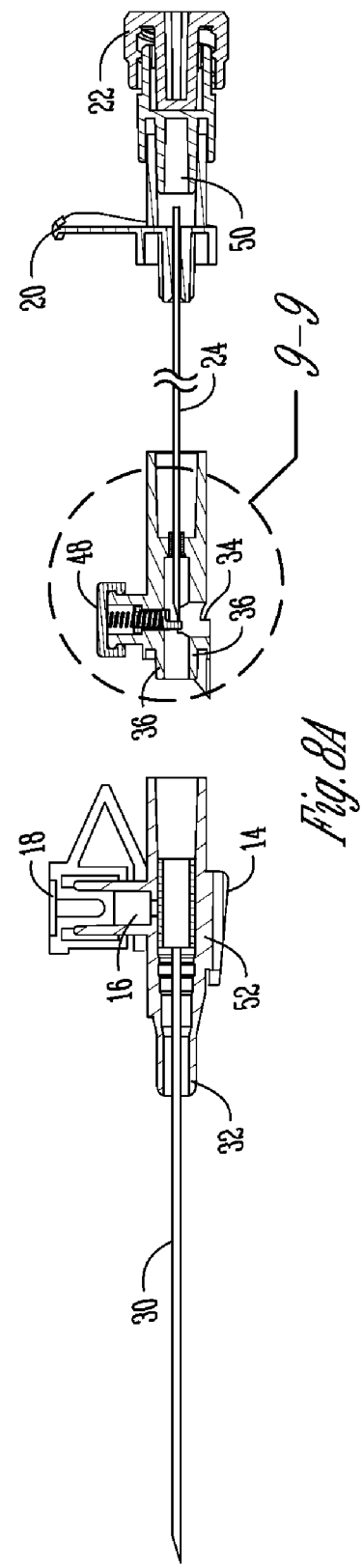
FIG. 8A is a cross sectional view of the apparatus of FIG. 8 taken along line 8A-8A.

FIG. 8 shows safety device 34, needle 24 and needle hub 20 in unitary assembly being detached from the wing housing 14.

FIG. 8A shows the safety device 34 covering the needle tip 26 separated from the wing housing 14. After the needle tip 26 is blocked by the tip blocker 42 as described in the proceeding paragraphs, upon further withdrawal of the needle 24, the needle flaring 28 comes in contact with the bush 40. Since the diameter of needle 24 is increased at the needle flaring 28, the bush 40 does not allow needle faring 28 to pass through the bush 40. Thus, the flaring 28 on the needle 24 cannot be pulled through the bush 40. If any further force is applied to pull the needle 24 out of the safety device 34, it detaches the lugs 36 attached to the wing housing 14, which detaches the safety device 34 from the wing housing 14.

Figure 9:
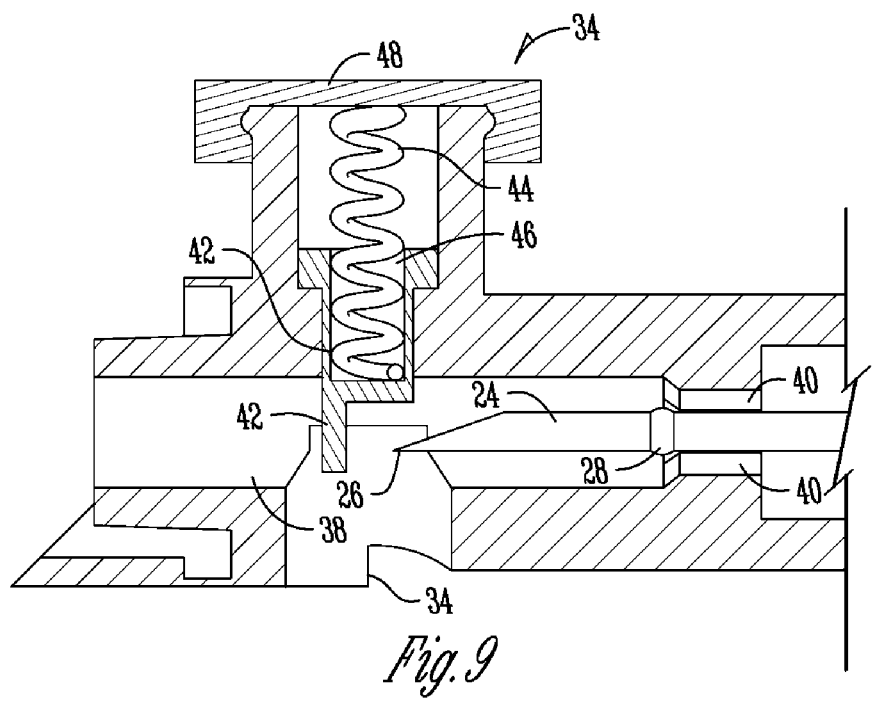
FIG. 9 is an enlarged view of section 9-9 of FIG. 8A.
Figure 9A:
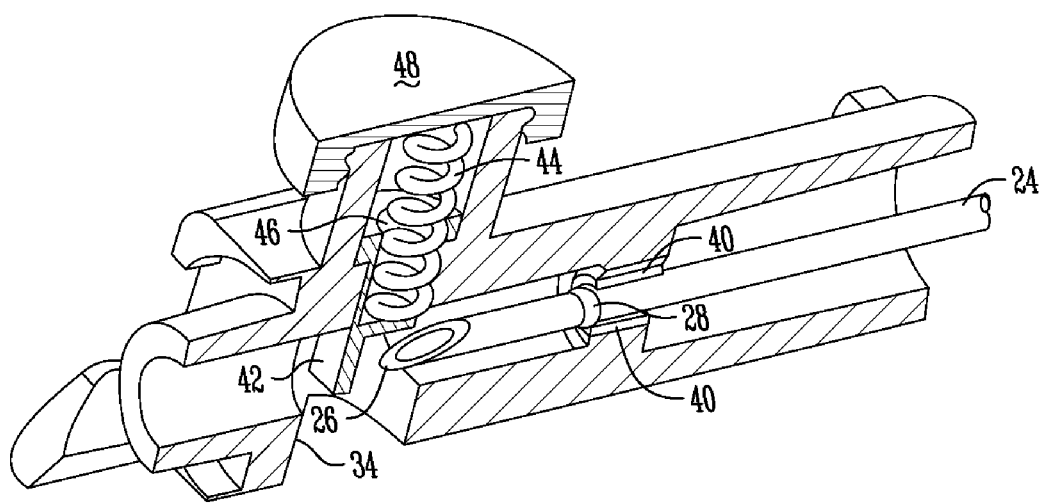
FIG. 9A is an isometric view of section 9-9 of FIG. 8A.

FIG. 9 shows the flaring 28 of the needle 24 in contact with the bush 40 on one side and tip blocker 42 blocking the needle tip 26 on the other side. Thus, the needle 24 cannot be pushed or pulled out of the safety device 34 as the needle tip 26 is locked within the safety device 34. FIG. 9A shows an isometric view of the safety device 34, namely tip blocker 42, needle tip 26, flaring 28, and bush 40.

The needle 24 with needle hub 20 on one end and safety device 34 on the other, as seen in FIG. 8, can be disposed of in a safe manner. Since the safety device 34 is made sufficiently large, it covers the needle tip 26 from all sides so that the infected needle tip 26 is not exposed from any side.

The bush 40 and tip-blocker 42 arrangement locks the needle tip 26 very securely so that the needle tip 26 does not accidentally slip out of the safety device 34.

As best shown in FIGS. 2, 3 and 8A, the safety device 34 of the present invention is an external attachment to the IV catheter apparatus 10, which detaches completely from the wing housing 14 after use, in such a manner that it does not affect the flow of fluids in the wing housing 14 and catheter 30.

The invention has been shown and described above with the preferred embodiments, and it is understood that many modifications, substitutions, and additions may be made which are within the intended spirit and scope of the invention. From the foregoing, it can be seen that the present invention accomplishes at least all of its stated objectives.

What is claimed is:

1. An intravenous apparatus comprising:
    a safety device;
    a wing housing;
    one or more lugs removably connecting the wing housing to the safety device whereby a pulling force applied to the safety device and the wing housing separates the safety device from the wing housing;
    an elongated needle passageway extending longitudinally through the safety device and the wing housing;
    a needle longitudinally movable in the needle passageway in a first direction and an opposite second direction, and comprising a needle tip longitudinally movable with the needle in the first direction from an exposed position wherein the needle tip is exposed to a patient's vein to a disposal position wherein the needle tip is within the safety device;
    a needle hub movable with the needle and in communication with the needle;
    a flash back chamber within the needle hub;
    a flare on the needle that is within the safety device when the needle is in the disposal position;
    a bush in the passageway within the safety device;
    wherein the flare and the bush prevent movement of the needle tip in the first direction within the passageway; and
    a needle tip blocker within the safety device and being movable relative to the passageway from a non-blocking position wherein the needle tip is free to move within the passageway to a blocking position wherein the needle tip is within the safety device and is blocked from returning within the passageway in the second direction.

2. The intravenous apparatus according to claim 1, further comprising a spring which engages the needle tip blocker and urges the needle tip blocker to the blocking position, and a disc holding the spring in place.

3. The intravenous apparatus according to claim 2 wherein the needle tip blocker comprises a groove, and the spring is at least partially disposed within the groove.

4. The intravenous apparatus according to claim 1, wherein the lugs are in friction fit with the wing housing, and wherein the pulling force overcomes the friction fit to thereby separate the safety device from the wing housing.

5. The intravenous apparatus according to claim 1, wherein the pulling force that separates the safety device from the wing housing is applied from the needle flare to the bush when the needle is moved in the first direction when the needle flare is in engagement with the bush.

* * * * *